(12) United States Patent
Miller et al.

(10) Patent No.: US 11,214,653 B2
(45) Date of Patent: Jan. 4, 2022

(54) WATER-SOLUBLE SOLID OR SEMI-SOLID DISPERSION OF PARTICLES

(71) Applicant: DUNE SCIENCES, INC., Eugene, OR (US)

(72) Inventors: John M. Miller, Eugene, OR (US); James Kasbohm, Eugene, OR (US); Richard T. Geiger, Eugene, OR (US)

(73) Assignee: DUNE SCIENCES, INC., Eugene, OR (US)

( * ) Notice: Subject to any disclaimer, the term of this patent is extended or adjusted under 35 U.S.C. 154(b) by 568 days.

(21) Appl. No.: 15/771,769

(22) PCT Filed: Oct. 28, 2016

(86) PCT No.: PCT/US2016/059579
§ 371 (c)(1),
(2) Date: Apr. 27, 2018

(87) PCT Pub. No.: WO2017/075534
PCT Pub. Date: May 4, 2017

(65) Prior Publication Data
US 2018/0346659 A1 Dec. 6, 2018

Related U.S. Application Data

(60) Provisional application No. 62/247,335, filed on Oct. 28, 2015.

(51) Int. Cl.
| | | |
|---|---|---|
| *C08J 3/00* | (2006.01) | |
| *C08J 3/05* | (2006.01) | |
| *A61L 9/012* | (2006.01) | |
| *C05D 9/00* | (2006.01) | |
| *A23L 29/00* | (2016.01) | |
| *C11D 3/00* | (2006.01) | |
| *A61L 9/14* | (2006.01) | |
| *A23P 10/30* | (2016.01) | |
| *C11D 3/02* | (2006.01) | |
| *C11D 3/12* | (2006.01) | |
| *A61K 8/02* | (2006.01) | |
| *C09C 1/00* | (2006.01) | |
| *A01N 59/16* | (2006.01) | |
| *A23L 2/52* | (2006.01) | |
| *C11D 3/20* | (2006.01) | |
| *A61K 33/38* | (2006.01) | |
| *A23L 33/16* | (2016.01) | |
| *A61K 8/29* | (2006.01) | |

(Continued)

(52) U.S. Cl.
CPC ................ *C08J 3/05* (2013.01); *A01N 59/16* (2013.01); *A23G 3/362* (2013.01); *A23L 2/52* (2013.01); *A23L 29/015* (2016.08); *A23L 33/16* (2016.08); *A23P 10/30* (2016.08); *A61K 8/0216* (2013.01); *A61K 8/044* (2013.01); *A61K 8/19* (2013.01); *A61K 8/29* (2013.01);
*A61K 33/38* (2013.01); *A61L 9/012* (2013.01); *A61L 9/14* (2013.01); *A61Q 13/00* (2013.01); *B01J 13/0043* (2013.01); *C05D 9/00* (2013.01); *C05D 9/02* (2013.01); *C07C 31/26* (2013.01); *C08K 3/08* (2013.01); *C08L 1/08* (2013.01); *C08L 5/08* (2013.01); *C08L 5/12* (2013.01); *C08L 29/04* (2013.01); *C08L 33/08* (2013.01); *C09C 1/00* (2013.01); *C11D 3/0068* (2013.01); *C11D 3/02* (2013.01); *C11D 3/1206* (2013.01); *C11D 3/1213* (2013.01); *C11D 3/2065* (2013.01); *A23V 2002/00* (2013.01); *A61Q 11/00* (2013.01); *A61Q 17/04* (2013.01); *B82Y 30/00* (2013.01); *C08K 2003/023* (2013.01); *C08K 2003/085* (2013.01); *C08K 2003/0806* (2013.01); *C08K 2003/0831* (2013.01); *C08K 2003/0843* (2013.01); *C08K 2003/0881* (2013.01); *C08K 2003/0893* (2013.01); *C08L 2201/54* (2013.01)

(58) Field of Classification Search
CPC .......... A23L 2/52; A23L 29/015; A23L 33/16; A23G 3/362; A23P 10/30; A01N 59/16; A61K 8/0216; A61K 8/044; A61K 8/19; A61K 8/29; A61K 33/38; A61Q 13/00; B01J 3/0043; C08J 3/05; C05D 9/00; C07C 31/26; C08K 3/08; C08L 1/12; C08L 29/04; C08L 33/08; C09C 1/00; C11D 3/0068; C11D 3/02; C11D 3/1206; C11D 3/1213; C11D 3/2065
USPC ................................. 516/77, 78, 97
See application file for complete search history.

(56) References Cited

U.S. PATENT DOCUMENTS

| | | |
|---|---|---|
| 9,149,440 B2 | 10/2015 | Turos et al. |
| 2007/0275969 A1 | 11/2007 | Gurny et al. |

(Continued)

FOREIGN PATENT DOCUMENTS

WO WO-2015049292 A2 * 4/2015 ............ A23L 33/10

*Primary Examiner* — Edward J Cain
(74) *Attorney, Agent, or Firm* — Schwabe, Williamson & Wyatt, P.C.

(57) ABSTRACT

Disclosed are solid or semisolid compositions the including finely divided particles and a water-soluble matrix that dissolves and disperses the particles when in contact with water. Also disclosed are kits for reducing and/or inhibiting odor formation on garment. The kit include one or more containers, wherein at least one of the one or more container includes solid or semisolid compositions the including finely divided particles and a water-soluble matrix that dissolves and disperses the particles when in contact with water. An edible silver delivery system including the compositions is disclosed as are methods of delivering silver to a subject in need thereof.

19 Claims, 3 Drawing Sheets

(51) Int. Cl.
    *A61Q 13/00*     (2006.01)
    *A61K 8/19*      (2006.01)
    *A23G 3/36*      (2006.01)
    *C05D 9/02*      (2006.01)
    *A61K 8/04*      (2006.01)
    *B01J 13/00*     (2006.01)
    *C07C 31/26*     (2006.01)
    *C08K 3/08*      (2006.01)
    *C08L 1/08*      (2006.01)
    *C08L 5/08*      (2006.01)
    *C08L 5/12*      (2006.01)
    *C08L 29/04*     (2006.01)
    *C08L 33/08*     (2006.01)
    *A61Q 17/04*     (2006.01)
    *A61Q 11/00*     (2006.01)
    *B82Y 30/00*     (2011.01)
    *C08K 3/02*      (2006.01)

(56) References Cited

U.S. PATENT DOCUMENTS

| | | |
|---|---|---|
| 2010/0112073 A1 | 5/2010 | Sabliov et al. |
| 2010/0119603 A1 | 5/2010 | Miller et al. |
| 2010/0239629 A1 | 9/2010 | Narayanan et al. |
| 2016/0242432 A1* | 8/2016 | Windhab .............. A23G 1/0006 |

* cited by examiner

Gum Drop/Gummy
(with or without sugar coating)

Cross-section
(showing amorphous or
cross-linked network composite 1)

Close-up of outside of gum drop
(Coated with silver/sugar
composite 2)

FIG. 7

WATER-SOLUBLE SOLID OR SEMI-SOLID DISPERSION OF PARTICLES

CROSS REFERENCE TO RELATED APPLICATIONS

The present application is a national phase entry under 35 U.S.C. § 371 of International Application No. PCT/US2016/59579, filed Oct. 28, 2016, entitled "WATER-SOLUBLE SOLID OR SEMI-SOLID DISPERSION OF PARTICLES," which designated, among the various States, the United States of America, and which claims priority to U.S. Provisional Patent Application No. 62/247,335 filed Oct. 28, 2015, both of which are hereby incorporated by reference.

TECHNICAL FIELD

This Application concerns finely divided particles, and specifically to the dispersion of these finely divided particles into aqueous environments.

BACKGROUND

Finely divided particles, for example sub-micron particles, including nanoparticles, and colloids are very small particles generally with a particle size typically in the range of 1 nm to 1000 nm. Due to their tiny size, finely divided particles have many unique and special properties/features related to their tiny size, and more specifically to their surface/volume relationship. Examples include catalytic properties, optical properties, mechanical properties, electrical properties, magnetic properties, and antimicrobial properties, among others. A colloid is typically thought of as any particles substantially larger than atoms or ordinary molecules but too small to be visible to the unaided eye and having at least one dimension in this general size range, which encompasses about $10^{-7}$ to $10^{-3}$ cm. (1-1000 nm). A dispersion of finely divided particles, such as a colloidal dispersion, is a mixture in which one substance of microscopically dispersed insoluble particles is suspended throughout another continuous phase substance, such as an aqueous environment.

In many cases, the utilization finely divided particles (e.g. colloidal particles and/or nanoparticles) in products and devices relies on the ability to controllably disperse these particles in relevant media, such as an aqueous environment within the system and to maintain this dispersion during and after product manufacturing. This task can prove to be quite challenging due to the intrinsic stability, or more specifically lack thereof, of the particles that want to aggregate, agglomerate, precipitate, or otherwise degrade over time due to intermolecular forces and a driving force to reduce surface energy within the system.

Figure 1A:
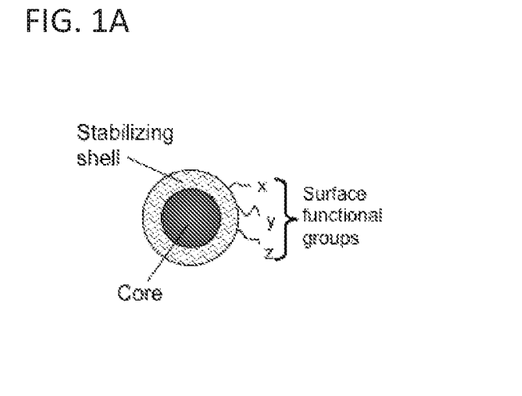
FIGS. 1A-1C are schematics showing examples of finely dispersed particles, nanoparticles, and colloidal particles.
Figure 1B:
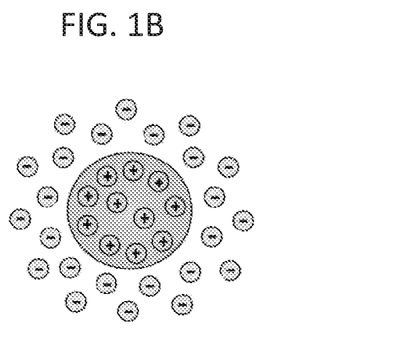
Figure 1C:
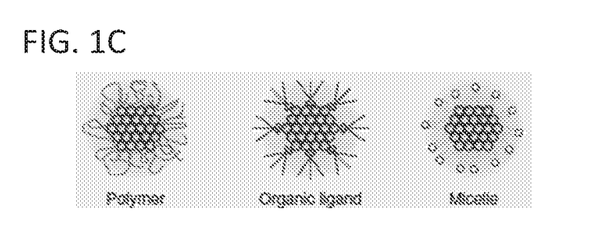

There have been significant numbers of reports that have focused on methods of liquid dispersion of finely divided particles. These include the use of steric repulsion and charge repulsion via stabilizers that are compatible with the system (see, for example, FIGS. 1A-1C). One approach to producing stable particle dispersion is to actually produce the particles via chemical reaction within the solvent system of choice using selected stabilizers and ligands. For example, metal particles can be produced via the chemical reduction of metal salt precursors in the presence of coordinating ligands in aqueous or organic solvents. Other approaches for chemical modification of particles have been widely reported in the literature.

While many of these approaches have worked for specific systems to disperse the particles in liquid formulations at the point of use, in many cases there remain significant challenges to maintain this dispersion so that the particles can be shipped to, and incorporated into, products at different production facilities, especially when used at higher concentrations. As an example, if an aqueous solution freezes or is subjected to extreme heat, the finely divided particles can become unstable and will not redisperse. Further, the transportation and handling of liquid solutions of the finely divided particles may require additional safety precautions and, in many cases, separate shipping containers.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

FIG. 1A, is an example of stabilized nanoparticles that are comprised of a core (metal, metal oxide, metal salt, quantum dot, etc.), a stabilizing shell (polymer, ligands, etc.) that provides either steric or charge stabilization in the liquid dispersion, and possibly additional ligands to provide additional features/benefits (e.g. antibodies that can provide targeting function, or solubility enhancers). FIG. 1B, is an example of colloidal particles that have little or no chemical stabilizers, but are stabilized through charge repulsion. FIG. 1C, is additional examples of stabilized particles with polymers, ligands, or micelles.

DETAILED DESCRIPTION OF DISCLOSED EMBODIMENTS

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense.

Various operations may be described as multiple discrete operations in turn, in a manner that may be helpful in understanding embodiments; however, the order of description should not be construed to imply that these operations are order-dependent.

The description may use perspective-based descriptions such as up/down, back/front, and top/bottom. Such descriptions are merely used to facilitate the discussion and are not intended to restrict the application of disclosed embodiments.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Figure 2:
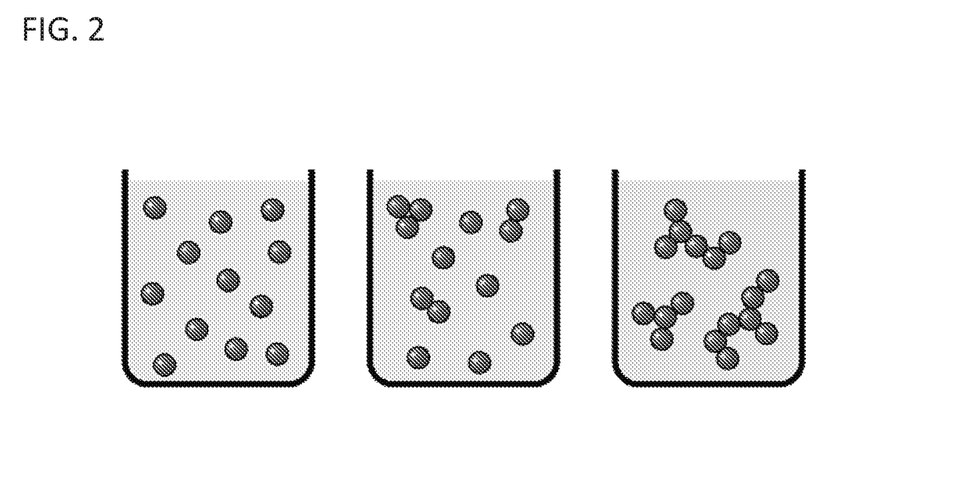
FIG. 2 is a schematic showing examples of aqueous dispersion of particles used in the manufacture of the water soluble composite particle formulations. As disclosed herein, the prefabricated dispersion of particles include systems in which solid particles or small aggregates of solid particles are dispersed in aqueous media in the form of a suspension, as stable colloids, or as a homogeneous solution. The concentration of the particles in the aqueous dispersion prior to producing the water soluble formula is in the range 1-10000 ppm.

This disclosure addresses the limitations of particle stability in aqueous solutions, such as those discussed above, by using solid or semisolid formulations that maintain the particle dispersion, but in a more easily handled form. As disclosed herein the particles can be controllably redispersed in aqueous solutions for point of use addition (see, for example, FIG. 2).

While special attention in this disclosure is given to finely divided silver particles, including colloidal silver and silver nanoparticles specifically, the present disclosure is equally applicable to any finely divided particles, such as nanoparticles, and/or colloids, in general. In other words, the compositions disclosed herein can be used to disperse finely divided particles, for example nanoparticles and/or colloids, composed of various materials in a non-limiting sense.

Figure 3:
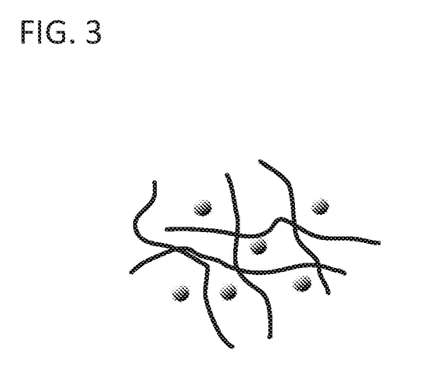
FIG. 3 is a schematic showing finely divided particles dispersed/encapsulated in water-soluble amorphous matrix. In this case, the particles are embedded within the amorphous matrix as happens in the case of using gelatin or pectin for semi-solid formulations or isomalt for solid formulations.
Figure 4:
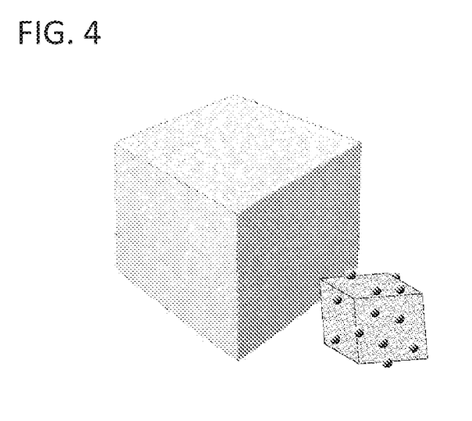
FIG. 4 is a schematic showing water-soluble "sugar cube" composite formula. In this case, the aqueous dispersion of particles is added directly to the sugar cube or the powder, and the particles coat the surface of the individual grains within the composite as shown in the enlargement of a single grain. Given the water soluble nature of the matrix, there may be some dissolution and reprecipitation of the matrix during processing.
Figure 5:
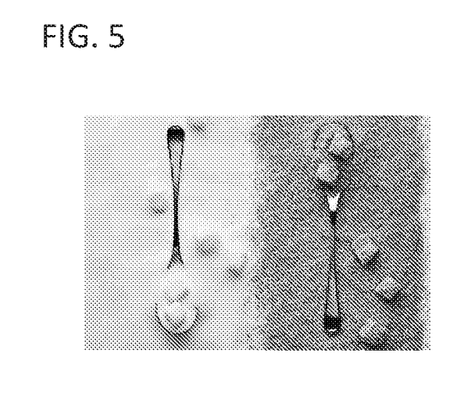
FIG. 5 is a digital image of water-soluble granular formula without (left) and with (right) dispersed particles. In this case, the particles have a dark brownish color.
Figure 6:
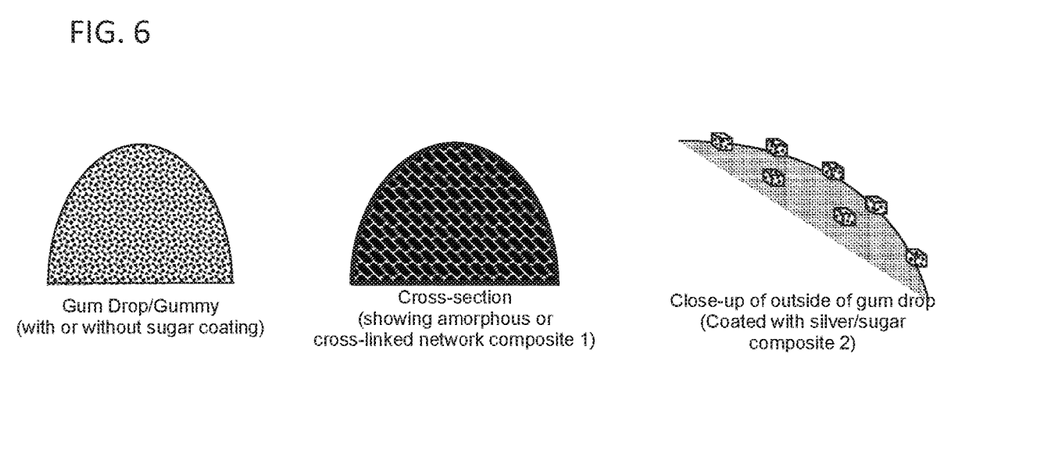
FIG. 6 are schematic representations of an edible silver delivery system in the form of a gum drop or gummy drop. Two different variations are shown, one with the silver embedded in the gelatin network (as in amorphous composite), and one showing the use of granular composite coating the outside of the gum drop.
Figure 7:
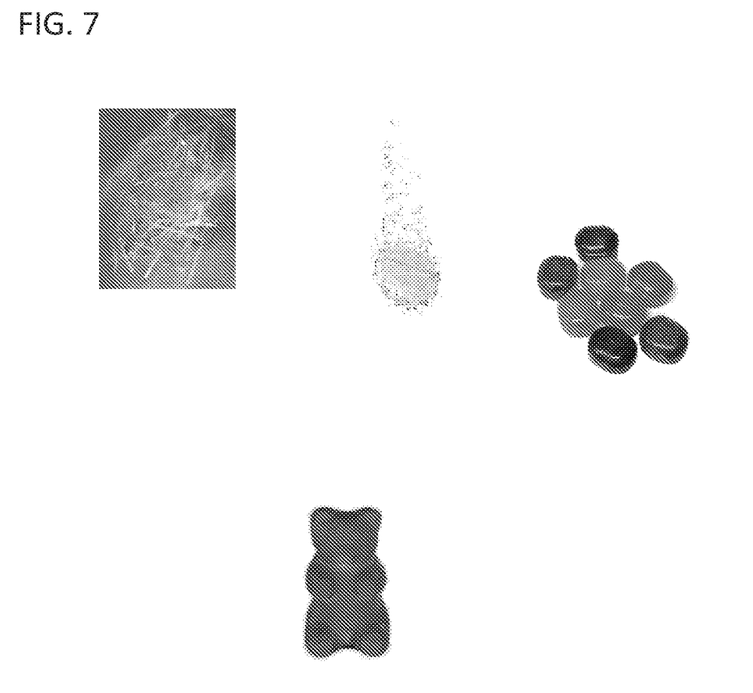
FIG. 7 is a set of digital images of other forms of edible silver, for examples, hard candy, effervescent tablet, pulled sugar, and a gummy.

As disclosed herein, the inventors have discovered and developed novel water-soluble solid or semi-solid composite formulations or compositions containing finely dispersed particles, for example colloidal particles, and/or nanoparticles. The disclosed formulations or compositions allow for controlled dissolution and dispersion of these particles in aqueous solutions. The formulations include prefabricated finely dispersed particles, for example colloidal particles, and/or nanoparticles, that are dispersed within and/or on the surface of a non-reactive water-soluble matrix (see, for example, FIGS. 3-5). Thus, disclosed is a solid or semisolid composition that includes finely dispersed particles, for example colloidal particles, and/or nanoparticles, and a water-soluble matrix that dissolves and disperses the particles when the matrix comes in contact with water. A water-soluble matrix can include both a fully dissolved matrix and water dispersible matrix, such as a hydrocolloid. In embodiments, a water-soluble matrix a material that is fully dissolved by an aqueous environment, and/or a material that water dispersible. While not being bound by operational theory, the inventors' discovered that using a water soluble matrix to physically separate the particles allows the particles to solvate and disperse into the aqueous solution as the matrix dissolves. By paring a water soluble matrix that does not specifically interact (e.g. non-specifically interacts, for example interacting via non-bonding, non-specific interactions between the particles and the water-soluble matrix, such as H-bonding, electrostatic interactions, van der Walls forces, and the like.) with particles, the particles can be released and/or dispersed into an aqueous solution. Using the disclosed compositions, this is done without forming large agglomerates that may cause the particles to crash out of solution. Thus, it is this combination of materials that gives the compositions disclosed herein the ability to release the particles into solution. In embodiments, the water soluble matrix dissolves and/or disperses upon contact with water. In embodiments, heat can be applied to the system to facilitate dissolution of the water soluble matrix.

One of the unique features of the disclosed formulations is the ability to produce a solid or semisolid dispersion of particles having less than 20% water by weight that can then be readily redispersed and formulated into products such that the particles do not appreciably aggregate when dry (unlike if they were simply dried without a supporting matrix). In certain embodiments, the finely divided particles are substantially uniformly dispersed within the water-soluble matrix. In certain embodiments, the finely dispersed particles remain substantially dispersed within the water-soluble matrix when dried or substantially dried (for example dried to less than about 20% water by weight)

As disclosed herein the compositions include one or more types of finely divided particles. In embodiments, a finely divided particle is a nanoparticle. In embodiments, a finely divided particle is a colloid. In embodiments, the particle diameter of the finely divided particles and/or nanoparticles is in the size range of about 1 nm to about 1000 nm, such as about 10 nm to about 100 nm, about 100 nm to about 500 nm, about 50 nm to about 700 nm and variations thereof. In embodiments, the particle diameter of the finely divided particles and/or nanoparticles is in the size range of about 1 nm to about 1000 nm. In some embodiments, the finely divided particles and/or nanoparticles is in the size range of about 100 nm to about 500 nm. In some embodiments, the finely divided particles, such as nanoparticles, are in the size range of about 1 nm to about 100 nm. The particles can be of various shapes, including but not limited to spheroids, rods, tubes, plates, cubes, prismatic, pyramidal, cages, dendrimers, and small agglomerates of these shapes.

In embodiments, the finely divided particles and/or nanoparticles are one or more of Ag, Au, Ti, Zn, Zr, Cu, Ni, Co, Fe, Al, Si, Sn, Ce, Pt and W, water dispersible metal oxides and sulfates thereof, water dispersible metal salts thereof, or combinations thereof. In certain embodiments, the finely divided particles and/or nanoparticles are quantum dots, for example a semiconductor material such as silicon, PbS, PbSe, lead selenide CdSe, CdS, InAs, InP/ZnS and CuInS/ZnS and the like. In certain embodiments, the finely divided particles and/or nanoparticles are carbon (C) including amorphous particles, fullerenes, nanotubes, graphitic, diamond or diamond-like, or graphene. In certain embodiments, the finely divided particles, and/or nanoparticles, are organic polymers, for example that can act as pharmaceutical/drug/payload delivery vehicles that encapsulate, entrap, coat, or otherwise attach drugs or other payloads to the polymer nanoparticle matrix. In embodiments, the finely divided particles include hydrophilic functionality on the surface (for example intrinsic functionality, or a surface modifier for hydrophobic particles). In embodiments, the finely divided particles, such as nanoparticles, include surface stabilizers or ligands that provide steric, charge, or other mechanisms of stabilization as well as additional function to the particles. In some embodiments, a finely divided particle includes a surface chemical group that enables, or increases, water dispersibility of the particles, for example, hydroxyl, amine, carboxylate, sulfate, and phosphate groups, among others. In some embodiments, the surface chemical group is intrinsic to the particle. In some embodiments, wherein the surface chemical group is added by functionalization, for example, either covalent or non-covalent modification of the particle.

As disclosed herein, the compositions include a water-soluble matrix. A desirable property of the matrices is non-reactivity, water dissolvable/dispersible, and having only non-specific interactions, such as hydrogen bonding, electrostatic interaction or van der Waals forces with the particles. Matrices suited for the dispersion of the finely divided particles include water soluble and/or dispersible polymers. The matrices can by formulated in many forms, for example solid granular powders, solid compactions of powders to produce a porous solid matrix, polymeric gels that encapsulate or otherwise stabilize the particles. In embodiments, a water-soluble matrix includes one or more water soluble polymers. Examples of water soluble polymers include water soluble polypeptides, polysaccharides, sugar alcohols, polyacrylic acid (PAA) and copolymers, polyvinyl alcohol, polyacrylamides (PAM), polyethylene glycols (PEG), polyamines and polyethyleneimines, quarternary ammonium polymers, and/or hydrocolloids, amongst others. As used herein, hydrocolloids are water soluble particles that include gelatin, certain polypeptide, and polysaccharides such as any of the gums, and synthetic molecules that can form particle-like dispersions in water. However, not all polysaccharides or polypeptides would be considered hydrocolloids. In certain embodiments, the matrices may be characterized as hydroxylated organic molecules and polymers including carbohydrates/saccharides (mono-, di-, and poly-) and hydrolyzed biopolymers. In embodiments, a water soluble polymer is a hydrocolloid, a polypeptide, a polysaccharide, and/or a sugar alcohol, or any combination thereof. In embodiments, a disclosed composition includes one or more of hydrocolloids of polypeptides, such as gelatin, and, a polysaccharide, such as one or more of carboxymethylcellulose, pectin, chitosan, agar, agarose, lactose, sucrose, glucose, and cyclodextrin and/or a sugar alcohol, such as one or more of mannitol, xylitol, erythritol, sorbitol, maltitol, lactitol, arabitol, ribitol, and isomalt. Thus, in embodiments, the water soluble/dispersible matrix is selected from one or more of polyacrylic acid (PAA) and copolymers, polyvinyl alcohol, polyacrylamides (PAM), polyethylene glycols (PEG), polyamines and polyethyleneimines, quarternary ammonium polymers, gelatin, carboxymethylcellulose, pectin, chitosan, agar, agarose, lactose, sucrose, glucose, cyclodextrins, mannitol, xylitol, erythritol, sorbitol, and isomalt, agar, alginate, arabinoxylan, carrageenan, cellulose, curdlan, gellan β-glucan, guar gum, gum Arabic, locust bean gum, starch, xanthan gum, polyacrylate and/or polyvinyl alcohol, or other similar materials.

In embodiments, the relative concentration of particles is about 0.01 percent by weight (wt %) to about 30 percent by weight although lower or higher concentration are contemplated. In certain embodiments, the particles are loaded onto a solid granular support at a concentration of about 1000 ppm (1000 mg particles/kg final product), or 0.1 wt %. In certain embodiments, the particles are loaded onto a solid granular support at a concentration of about 15000 ppm (15000 mg particles. In certain embodiments, the finely divided particles coat the surface of the water-soluble matrix. In embodiments, wherein the finely divided particles coat the surface of the water-soluble matrix they are dispersed so that the particles do not aggregate, agglomerate, or otherwise irreversibly stick together to prevent dissolution. In embodiments, the finely divided particles are substantially uniformly dispersed within the water-soluble matrix and are dispersed so that the particles do not aggregate, agglomerate, or otherwise irreversibly stick together to prevent dissolution.

In embodiments, the final moisture content of a disclosed composition, such as a dried composition, is between about 0.1% and about 20%, such as about 0.1%, 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, 10.0%, 11.0%, 12.0%, 13.0%, 14.0%, 15.0%, 16.0%, 17.0%, 18.0%, 19.0%, and 20.0%, for example, about 0.1% to about 1.0%, about 0.5% to about 5.0%, about 0.1% to about 10.0%, about 1.0% to about 15.0%, about 5.0% to about 20.0%, and the like.

In embodiments, the composition is in the physical form of powder, pressed-powder forms, cross-linked monoliths, gel structures, gummy structures, tablets, and porous compactions, granular, films, and/or fibers. In addition to the basic water soluble formulation included of fine particles, such as nanoparticles, dispersed in a water soluble matrix, the compositions may include the addition/incorporation of other ingredients (excipients) including humectants, binders, colorants, flavorants, pH control, texture and consistency modifiers, fillers, preservatives, scents, activators, stabilizers, health supplements, and pharmaceutical ingredients, vitamins and other dietary etc. into the formulation for additional product features and benefits. In embodiments, the unit packaging allows for controlled dosing of the finely divided particles or nanoparticles and/or the material in the compositions.

Also disclosed herein are kits, for example for reducing and/or inhibiting odor formation on garment. In embodiments a kit includes one or more containers, wherein at least one of the one or more containers includes a disclosed composition of finely divided particles and/or nanoparticles and a water soluble matrix, such as embedded or and/or within the matrix. In embodiments, at least one of the one or more containers includes a buffering agent. In embodiments, the buffering agent includes a citrate salt. In embodiments, at least one of the one or more containers includes a detergent. In embodiments, the kit further includes directions for using the kit. In embodiments, the one or more containers include a first container including the composition, a second container including a buffering agent and a third container including a detergent. In embodiments, the finely divided particles and/or nanoparticles of the composition include Ag or an oxide or salt thereof and the water-soluble matrix of the composition includes mannitol.

While a focus of this disclosure is on delivery of silver-based colloids and for use in a laundry product formulation, the disclosed technology can be applied to a wide variety of finely-dispersed particles that can be dispersed in water and used for a wide variety of applications including pigments, water purification, aqueous inks, surface coatings and paints, pesticides, fertilizers, environmental waste/contamination remediation, dietary supplements, pharmaceutical delivery, therapeutic agents, wound care treatment, cosmetics, solar cells and other energy storage and conversion devices, and cleaning products, among others.

Also disclosed herein are edible versions of solid or semisolid finely divided particles, for example for use in dispersing the particles within the human body. In some disclosed embodiments, are edible versions of solid or semisolid colloidal silver for use as a dietary supplement.

For many years, silver was employed as a germicide and an antibiotic before modern antibiotics were developed. In previous centuries, users would shave silver particles into their drinking water, or submerge whole silver pieces in the drinking water, for the purpose of ingesting the silver by drinking the water. Thus, it seems likely that the practice of eating with silver utensils (i.e., silverware) resulted from a belief in the healthful properties of silver. More recently, with the increase in antibiotic resistant strains of bacteria and more public awareness about infection and health, the broad spectrum antibacterial and antifungal properties of silver have led to its use in an assortment of medical and consumer products. The vast majority of commercial applications of silver as an antimicrobial/anti-odor agent focus on either 1) topically applied salves, bandages, and medical devices, or 2) treated inanimate objects such as clothing, water filters, etc. that do not make public health claims but rather protect the article itself. However, oral consumption of silver, particularly in the form of dilute aqueous colloidal silver solutions, is widely practiced to help restore internal health as evidenced by the wide variety of health food grocers, pharmacies, and supplement stores that sell multiple brands of colloidal silver.

Colloidal silver is comprised of metallic silver particles that are stabilized (either by charge or by sterics) in aqueous solutions. These silver colloids slowly oxidize and release ionic silver that can deliver the antibacterial and antimicrobial properties to the system. Colloidal silver is widely sold as a drinkable aqueous liquid and requires measurement of the dosage with a teaspoon. In a typical colloidal silver solution, the daily dosage recommendations are 1 teaspoon or 5 ml of the aqueous solution which is generally 10 ppm (or 10 µg/ml). Hence a unit dosage would be 50 µg/day. However, the ingestion of too much silver, over time, may lead to discoloration of the skin in a condition known as Argyria. Poor control over the dosage of silver can increase the likelihood for development of these conditions. Further, bottles of aqueous colloidal silver are not practical for travel due to current regulations regarding liquids in addition to the added weight of the water. However, no solid or semi-solid form of edible silver as described herein is available.

Disclosed herein are edible silver delivery systems. In embodiments, the edible silver delivery systems include finely divided particles, such as colloids and/or nanoparticles, of colloidal and/or ionic silver; and a water-soluble matrix that dissolves and disperses the particles when in contact with water. This delivery method allows for precise unit dosing of the silver in a fully ingestible form in which the silver is fully dispersed upon dissolution in the mouth/body or in a beverage. In embodiments, the silver source used to produce the edible form of silver includes: colloidal silver, stabilized silver nanoparticles, and/or ionic silver. In embodiments, the colloidal and silver particles are in the size range of about 1 nm to about 100 nm. In embodiments, the colloidal and silver nanoparticles may include spheroidal, prismatic, rod-like, cubic particles. In embodiments, the silver content controls the unit dosing in the range of about 1 µg Ag/dose to about 1000 µg Ag/dose. The form of the new formula includes powders, gels, gummy, porous powder compacts such as sugar cubes, or amorphous solids such as hard candy. These forms can be unit packaged to control the amount of particles provided to a system. In embodiments, the edible silver delivery system is as a confectionery including hard candy, a gummy, a spun sugar (cotton candy), or a fast dissolving tablet that can be added to beverage for oral consumption. This delivery method allows for precise unit dosing of the silver in a fully ingestible form and in which the silver is fully dispersed upon dissolution in the mouth/body or in a beverage.

Also disclosed are methods for delivery of silver to a subject in need thereof, comprising selecting a subject in need; and administering an effective amount of the edible silver delivery system to the subject.

A method for producing edible silver delivery system is disclosed. The method includes the formation of a silver-matrix composite followed by subsequent blending with additional formulating agents to produce a flavorful health supplement.

EXAMPLES

Example 1

This example describes methods of forming a composition that includes nanoparticles dispersed in a water soluble matrix as disclosed herein.

For a crystalline or granulated solid in the form of powder or compressed powder pellets, cubes, etc., the disclosed compositions uses the method of incipient wetness to disperse the particles in the matrix. Incipient wetness impregnation (IW or IWI), also called capillary impregnation or dry impregnation, uses capillary action to draw the solution into the pores of the matrix, whether it be a granular powder or monolithic form (sugar cube). However, unlike traditional IW, the matrix itself is soluble in the aqueous media, so the maximum absorption capacity depends on the solubility of the matrix as well as the pore volume. In examples, the materials disclosed herein are prepared using incipient wetness impregnation with an aqueous dispersion of the finely divided particles nanoparticles.

The room temperature aqueous liquid is metered into dried non-reactive matrix powder or porous compact powder form at a ratio of 1 part water to 5 parts powder by spray, dropper, or other application device. In examples, this ratio can be as high as 20 parts powder to 1 part aqueous particle solution, or as low as 2 parts powder to 1 part aqueous dispersion. The particles are thoroughly blended with matrix powder for uniformity. The resulting mixture is post dried to the desired moisture content. The maximum liquid volume and particle concentration in that liquid determines the maximum loading of particles that can be achieved for a given sample. Excipient ingredients can be added prior to particle solution addition or after, provided they do not compromise the structure and moisture requirements.

Example 2

This example describes specific working formulations of the disclosed compositions.

Examples formulations used an aqueous dispersion of silver particles (0.9 wt % in water). The particles were stabilized in solution by a non-ionic surfactant, polysorbate, that is present in 0.25-0.30 wt. % of the aqueous dispersion. Prior to dispersion of the particles, an additional non-ionic surfactant was added at up to 10 wt. % to the liquid suspension. The additional surfactant was not required but aids in the drying process. The liquid suspension was then added slowly and while mixing to mannitol powder at a rate of 0.12 kg/kg of mannitol. Mannitol is a non-hygroscopic powder which will not absorb moisture. This mixture was then dried and sifted.

Example 3

This example describes the formation of an amorphous solid: e.g. spun or pulled sugar, etc., for example Ag Particles encapsulated in spun or pulled sugar.

Heat isomalt by itself or with 0-25% of water up to its melting point. Continue heating to 340 F, remove from heat. With vigorous stirring, add aqueous solution of finely divided particles with up to 16 wt. % (total) of the aqueous solution. Add excipient ingredients. Either pour into mold, spin the sugar, or pull into strands. Cool to room T.

Example 4

This example describes the formation of a semi-solid: e.g. gels, gummy, etc., for example Ag particles entrapped in gelatin/sugar matrix.

Add gelatin to aqueous dispersion of finely divided particles at desired concentration. Let hydrate for 5 minutes. Heat Solution to 50 C, let stir for 5-10 mins until all gelatin is fully dissolved. Add excipient ingredients to particle solution and blend until uniform. Pour into molds and let cool at room T or in refrigerator. Use between 10-50 wt. % gelatin (which includes total weight of water in aqueous dispersion.) Use different bloom strength to affect dissolution rate.

A preferred embodiment of the delivery system is a gummy-like formula included of a composite silver-gelatin component blended with sucrose, sorbitol, corn syrup and flavoring in the following ratios:

Gelatin: 10.7 wt. %
Silver 0.0025 wt. %
Water 19.9 wt. %
Sucrose: 31 wt %
Sorbitol: 3.1 wt. %
Corn syrup: 33.8 wt %
Natural or artificial flavoring oil: 1.5%

Example 5

This example describes the formation of a semi-solid, for example colloidal Ag particles, entrapped in a polyvinyl alcohol (pvOH) matrix.

A 4% solution of pvOH, mw. 85,000-124,000, 96% hydrolyzed, in water was prepared. To prepare, water was heated to 90 degrees C. and the pvOH was slowly added while stirring. The resultant was cooled to room T. In a separate container, a 4% solution of sodium borate in water was prepared by adding the sodium borate powder to water at room T. An aqueous dispersion of colloidal silver (4500 ppm) was added to the solution of pvOH in a ratio of 1 part colloidal silver to 9 parts 4% pvOH solution. The solution was mixed thoroughly. One part sodium borate solution (4%) was added to the pvOH/colloidal silver mixture. The solution was allowed to set to form the semisolid formulation that can then be subsequently dried in air. The resulting formulation can be subsequently dissolved in warm water.

Example 6

This example describes the formation of a solid dispersion of citrate stabilized gold nanoparticles on sugar alcohols. Citrate stabilized gold nanoparticles are widely used for optical detection of antibody-antigen reactions and other colorimetric assays. While they are straightforward to produce, they cannot be dried and resuspended due to irreversible aggregation of the particles.

Solutions of citrate-stabilized gold nanoparticles were prepared or obtained at a concentration of at least 1 mg/ml. 1 part gold nanoparticle solution that titrated to 9 parts granular solid sugar alcohol support including mannitol, sorbitol, etc. while blending. Residual moisture was removed by drying in desiccating oven at 40 degrees C. The resulting powder can then be readily redispersed in aqueous solutions at the desired concentration showing identical spectral absorption to the solution prior to drying.

Example 7

This example describes the formation of $TiO_2$ particles supported on granular sugar alcohol supports. $TiO_2$ is widely used in cosmetic formulations including sunscreen and other products. Depending on the size and source of the $TiO_2$ particles, it can be difficult to achieve uniform dispersion of the particles during formulation. The use of water dispersible formulations of the $TiO_2$ particles themselves as ingredients for cosmetic formulations can improve product quality and performance.

A dispersion of $TiO_2$ in water with up to 10 wt % $TiO_2$ was prepared. In some examples, the dispersion of the $TiO_2$ depends on particle size and surface chemistry and requires a combination of surfactants, imparted energy in the form of stirring, grinding, or ultrasonic agitators, and co-solvents to fully disperse. Once the dispersion was achieved, the solution was immediately titrated onto a granular solid sugar alcohol, which in some examples was mannitol, in a ratio of 1 part $TiO_2$ solution and 9 parts sugar alcohol while blending. The wet powder was at 40 C until moisture content was <1 wt %. This product can then be immediately redispersed for future formulation.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

We claim:

1. A solid or semisolid composition, comprising:
   finely divided particles; and
   a water-soluble matrix that dissolves and disperses the particles when in contact with water, wherein the moisture content of the matrix is in the range or between about 0.1% and 20% by weight, wherein the water-soluble matrix comprises a hydrocolloid.

2. The composition of claim 1, wherein the water-soluble matrix comprises one or more water soluble polymers.

3. The composition of claim 2, wherein the one or more water soluble polymers comprises one or more of biopolymers, polysaccharides, sugar alcohols, polyacrylic acid (PAA) and copolymers, polyvinyl alcohol, polyacrylamides (PAM), polyethylene glycols (PEG), polyamines and polyethyleneimines, and/or quarternary ammonium polymers.

4. The composition of claim 3, wherein the polysaccharides comprise one or more of carboxymethylcellulose, pectin, chitosan, agar, agarose, lactose, sucrose, glucose, cyclodextrins, alginate, arabinoxylan, carrageenan, cellulose, curdlan, gellan, β-glucan, guar gum, gum Arabic, locust bean gum, starch, xanthan gum, and polyacrylate.

5. The composition of claim 3, wherein the sugar alcohols comprise one or more of mannitol, xylitol, erythritol, sorbitol, isomalt.

6. The composition of claim 1, wherein the finely divided particles are substantially uniformly dispersed within the water-soluble matrix such that the particles do not appreciably aggregate, agglomerate, or otherwise irreversibly stick together to prevent dissolution.

7. The composition of claim 1, wherein the finely divided particles coat the surface of the water-soluble matrix and are dispersed such that the particles do not aggregate, agglomerate, or otherwise irreversibly stick together to prevent dissolution.

8. The composition of claim 1, wherein the finely divided particles include hydrophilic functionality on the surface.

9. The composition of claim 1, wherein the composition is in the physical form of powder, pressed-powder form, cross-linked monolith, gel structure, gummy structure, tablets, polymeric or a porous compaction.

10. A solid or semisolid composition, comprising:
    finely divided particles; and
    a water-soluble matrix that dissolves and disperses the particles when in contact with water, wherein the moisture content of the matrix is in the range or between about 0.1% and 20% by weight, wherein the finely divided particles comprise one or more Ag, Au, Ti, Zn, Zr, Cu, Ni, Co, Fe, Al, Si, Sn, Ce, Pt and W, water dispersible metal oxides and sulfates thereof, water dispersible metal salts thereof, or combinations thereof.

11. A solid or semisolid composition, comprising:
    finely divided particles; and
    a water-soluble matrix that dissolves and disperses the particles when in contact with water, wherein the moisture content of the matrix is in the range or between about 0.1% and 20% by weight, wherein the finely divided particles comprise quantum dots.

12. A solid or semisolid composition, comprising:
    finely divided particles; and
    a water-soluble matrix that dissolves and disperses the particles when in contact with water, wherein the moisture content of the matrix is in the range or between about 0.1% and 20% by weight, wherein the finely divided particles comprise carbon (C) including amorphous particles, fullerenes, nanotubes, graphitic, diamond or diamond-like, or graphene.

13. The composition of claim 1, wherein the finely divided particles comprise organic polymers.

14. A solid or semisolid composition, comprising:
    finely divided particles; and
    a water-soluble matrix that dissolves and disperses the particles when in contact with water, wherein the moisture content of the matrix is in the range or between about 0.1% and 20% by weight, wherein the particle diameter of the finely divided particles is in the size range of about 1 nm to about 1000 nm.

15. The composition of claim 1, further comprising one or more of humectants, binders, colorants, flavorants, scents, pH control, texture and consistency modifiers, activators, fillers, preservatives, stabilizers, health supplements, and pharmaceutical ingredients.

16. A kit for reducing and/or inhibiting odor formation on garment, comprising:
    one or more containers, wherein at least one of the one or more containers comprises a solid or semisolid composition, wherein the composition comprises finely divided particles, and a water-soluble matrix that dissolves and disperses the particles when in contact with water, wherein the moisture content of the matrix is in the range or between about 0.1% and 20% by weight.

17. The kit of claim 16, wherein at least one of the one or more containers comprises a buffering agent.

18. The kit of claim 16, wherein the one or more containers comprise a first container comprising the composition, a second container comprising a buffering agent, and a third container comprising a detergent.

19. The kit of claim 16, wherein the finely divided particles of the composition comprise Ag, an oxide, or salt thereof and the water-soluble matrix comprises mannitol.

* * * * *